(12) United States Patent
Patil

(10) Patent No.: US 6,171,496 B1
(45) Date of Patent: Jan. 9, 2001

(54) ANTIMICROBIAL FILTER CARTRIDGE

(75) Inventor: Arvind S. Patil, Davidson, NC (US)

(73) Assignee: Microban Products Company, Huntersville, NC (US)

(*) Notice: Under 35 U.S.C. 154(b), the term of this patent shall be extended for 0 days.

(21) Appl. No.: 09/246,509

(22) Filed: Feb. 9, 1999

Related U.S. Application Data

(63) Continuation-in-part of application No. 08/877,080, filed on Jun. 17, 1997, now Pat. No. 5,868,933, which is a continuation-in-part of application No. 08/573,067, filed on Dec. 15, 1995, now Pat. No. 5,762,797.

(60) Provisional application No. 60/090,996, filed on Jun. 29, 1998.

(51) Int. Cl.[7] .................................................. B01D 29/50

(52) U.S. Cl. ............... 210/484; 210/321.88; 210/321.89; 210/321.9

(58) Field of Search ........................... 210/500.23, 321.6, 210/321.78, 321.8, 321.79, 321.81, 321.9, 321.87, 321.88, 321.89, 636, 484, 488, 489; 264/48, 49, 162, 283; 428/198

(56) References Cited

U.S. PATENT DOCUMENTS

| | | | |
|---|---|---|---|
| 4,013,564 | * 3/1977 | Nose | 210/321.87 |
| 4,045,851 | * 9/1977 | Ashare et al. | 210/321.79 |
| 4,578,190 | * 3/1986 | Fowler | 210/321.89 |
| 5,032,269 | * 7/1991 | Wollbeck et al. | 210/321.8 |
| 5,071,551 | * 12/1991 | Muramatsu et al. | 210/266 |
| 5,198,110 | * 3/1993 | Hanai et al. | 210/321.69 |
| 5,498,468 | * 3/1996 | Blaney | 428/198 |
| 5,604,012 | * 2/1997 | Okamoto et al. | 210/500.23 |
| 5,693,230 | * 12/1997 | Asher | 210/321.79 |
| 5,762,797 | * 6/1998 | Patrick et al. | 210/497.1 |
| 5,762,798 | * 6/1998 | Wenthold et al. | 210/500.23 |
| 5,840,343 | * 11/1998 | Hall, II et al. | 424/616 |
| 5,868,933 | * 2/1999 | Patrick et al. | 210/484 |

FOREIGN PATENT DOCUMENTS

| | | | |
|---|---|---|---|
| 1156574 | * 6/1989 | (JP) | 210/500.23 |
| 2048024 | * 2/1990 | (JP) | 210/500.23 |

* cited by examiner

*Primary Examiner*—A. Fortuna
(74) *Attorney, Agent, or Firm*—Dougherty & Associates

(57) ABSTRACT

An antimicrobial microfiltration filter is made from a bundle of polymeric semipermeable hollow fibers treated with an antimicrobial agent and a microporous filter medium which may also be treated with an antimicrobial agent.

24 Claims, 1 Drawing Sheet

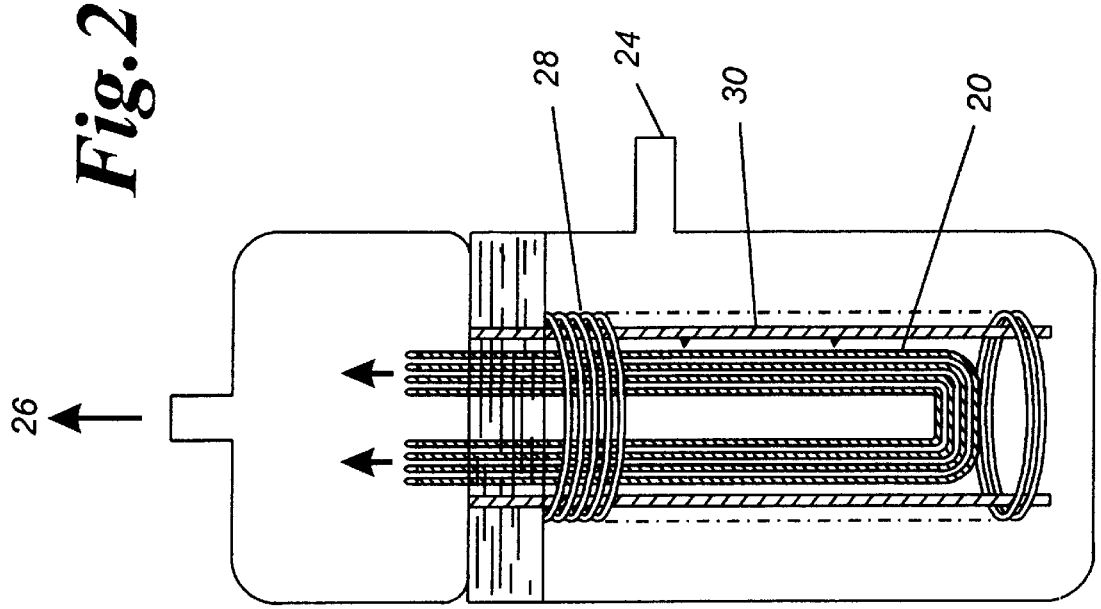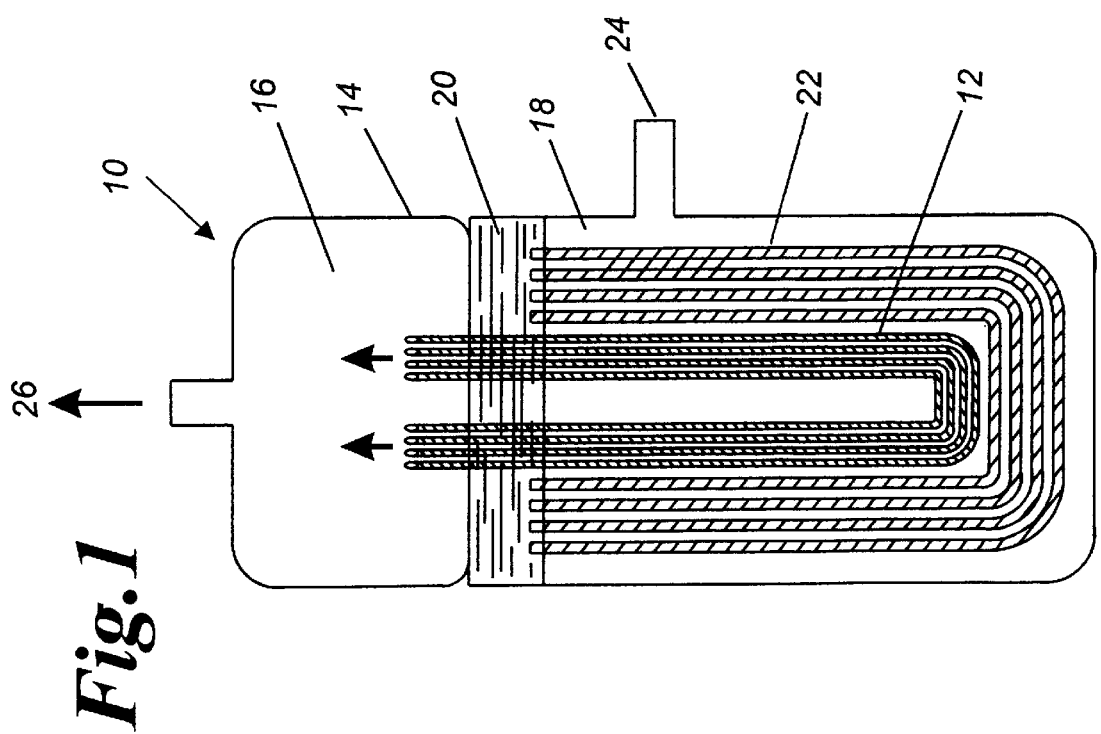

ANTIMICROBIAL FILTER CARTRIDGE

CROSS-REFERENCE TO RELATED APPLICATION

This application is a continuation-in-part of U.S. patent application Ser. No. 08/877,080, filed Jun. 17, 1997, now U.S. Pat. No. 5,868,933 which is in turn a continuation-in-part of Ser. No. 08/573,067 filed Dec. 15, 1995, now U.S. Pat. No. 5,762,797. This application also claims priority from provisional U.S. patent application Ser. No. 60/090,996 filed Jun. 29, 1998.

FIELD OF THE INVENTION

The present invention relates generally to filters for the purification of liquids. In particular, the invention relates to antimicrobial semipermeable hollow fiber membranes used in reverse osmosis, ultrafiltration/nanofiltration and microfiltration.

BACKGROUND OF THE INVENTION

In recent years, the public has become increasingly aware of the deteriorating quality and quantity of our nation's and the world's fresh water supply. Pollutants, biological and toxic waste and other contaminants are being introduced into water supplies at an ever increasing rate, making such water supplies unfit for drinking and other necessary uses. For example, medical patients with low immunity are now being requested not to drink tap water, and disease and illnesses linked to poor quality drinking water have increased dramatically in recent years. This problem is especially significant outside the United States where water quality has deteriorated to an all time low, with the major source of such contamination primarily being bacterial in nature.

In many areas of the world potable water is not only contaminated but it is also scarce. In these areas people must rely upon expensive purification systems to remove dissolved solids from sea water or well water.

Reverse osmosis filtration systems are some of the most common solutions for improving water quality. Osmosis is the flow or diffusion that takes place through a semipermeable membrane (as in a living cell) typically separating either a solvent (as water) and a solution or a dilute solution and a concentrated solution. The semipermeable membrane controls the flow of solute from the concentrated solution to the dilute solution thus bringing about conditions for equalizing the concentrations of solute on the two sides of the membrane to form an equilibrium. In reverse osmosis, pressure is deliberately applied to the more concentrated solution causing the flow of solvent in the opposite direction through the membrane, i.e., into the more dilute solution. In this way the liquid can be separated from solids and dissolved solids, decreasing the concentration of the solids and dissolved solids in the filtered fluid.

The wide spread use of reverse osmosis to produce potable water began in the early 1960's when Loeb and Sourirajan developed thin-skin cellulose acetate membranes for use in reverse osmosis systems. These cellulose acetate membranes provided much higher salt rejection (approaching 95%) and solvent flow than previously known reverse osmosis methods. Cellulose acetate membranes are also relatively inexpensive and are very tolerant of chlorine which is commonly used to eliminate bacteria in water. Since the 1960's the use of reverse osmosis has grown dramatically in waste water applications and industrial desalinization plants to produce drinking water from brackish and sea waters. More recently cellulose acetate membranes have been incorporated into consumer filtration systems to produce drinking water at the point of use. Matsuura, T., Synthetic Membranes and Membrane Separation Processes, CRC Press, (1994). Although cellulose acetate membranes greatly expanded the utilization of reverse osmosis treatment systems, such systems are still restricted by operational problems. For example, cellulose acetate membranes biodegrade readily.

Recently, thin film composite polyamide membranes have been developed that offer better performance than cellulose acetate membranes. These composite polyamide membranes exhibit salt rejection rates greater than 99.5% at pressures much lower than the pressures used for cellulose acetate membranes. Additionally, polyamide membranes reject silica, nitrates, and organic materials much better than cellulose acetate membranes. Because of the high performance of composite polyamide membranes, these membranes are used in high purity or ultrahigh purity water systems in pharmaceutical and electronics industries. However, just as cellulose acetate membranes exhibit a limiting characteristic (i.e., biodegradation) so do composite polyamide membranes. Composite polyamide membranes are susceptible to damage from chlorine.

As the technology for manufacturing composite polyamide and cellulose acetate membranes has progressed, new fields of filtration, called ultrafiltration (also called nanofiltration) and microfiltration have been created. Membranes based on polysulfone, polycarbonate, polypropylene, polyvinylidene difluoride and nylon have been developed for these applications.

For example, membranes used in hyperfiltration remove particles of 1–10 Angstrom units and include chemical compounds of about 180 to 15,000 molecular weights. Ultrafiltration filters particles of 30 to 1,100 Angstrom units that includes macromolecules of molecular weight of 10,000 to 250,000. Microfiltration which is mainly used to remove bacteria from solutions covers the range of 500 Angstrom to 20,000 Angstroms or 0.05 to 2 microns. (Lonsdale, H. K. "The Growth of Membrane Technology" Journal of Membrane Science, 10, p.80–81 (1982)). Unfortunately, these great strides in filtration have come at a cost, primarily in the form of bacteria contamination of filters and increased back pressures.

Bacteria contained in influent water may be arrested by reverse osmosis filters. In such a filter bacteria accumulate on the surface of the semipermeable membranes. Bacteria multiply every 30–60 minutes. Their growth is logarithmic and a single bacterial cell will result in 16 million bacteria in 24 hours. The explosive growth of bacteria results in fouling of the membrane which reduces the flow of water through the membrane and can adversely affect the filtering properties of the membrane. For example, bacteria build-up typically has an adverse affect on salt rejection in a reverse osmosis membrane. (Wes Byrne, Reverse Osmosis, Chapter 9- Biological Fouling). Fouled membranes require higher operating pressures which in turn increases operating costs.

In addition to reducing water quality and pressure, bacteria fouled membranes are difficult to clean. As a result of bacterial growth on the membrane, a gelatinous biofilm is formed on the upstream surface of the membrane which is very difficult to remove, except through use of strong chemical oxidants that damage the membrane. The biofilm protects the bacteria from the normal cleaning and sanitizing procedures and leads to a break through of bacteria across the membrane. This phenomena is not completely understood, since the pores of most reverse osmosis and ultrafiltration membranes are at least 2 to 4 orders of magnitude smaller than the bacterial cells. One possible explanation is that the bacterial cells exist in a dynamic state with continuous morphological changes occurring throughout the population. These bacteria then get more opportunities and time to find their way to an accommodating pathway through the membrane. Typically, bacteria are detected on the downstream side of the membrane in 48 to 72 hours. The downstream side of the membrane becomes discolored or black over time as the bacteria colonize on the downstream side of the membrane and form a biofilm that is difficult to remove. Such biological fouling can also lead to formation of localized extremes in pH that can damage the membrane.

The filter cartridges described in U.S. Pat. No. 5,762,797; application Ser. No. 08/877,080 and application Ser. No. 60/090,966 provide solutions to the problems created by bacteria buildup in reverse osmosis filters. By incorporating antimicrobial agents within various structures within the filter, water filters may be produced that are capable of removing and eliminating practically all microorganisms that may be present in the influent.

However, these filters, especially those with smaller pore sizes, create substantial back pressures in water delivery systems. In many countries the water pressure in municipal water lines is less than 60 psi. In such countries 0.1 to 0.45 micron rated filters, such as those described in U.S. Pat. No. 5,762,797, result in flow rates too low for practical operation. To address this problem the continuation application, Ser. No. 08/877,080, taught among other things, the use of a filter cartridge with semipermeable membranes having a nominal pore size of 0.75 microns. Increasing the nominal pore size increases the flow of the water through the filter cartridge without increasing back-pressures.

Unfortunately, increasing the nominal pore size of a filter also compromises the filter's ability to retain and deactivate bacteria. For example, some bacteria may slip through pores of 0.75 microns. In theory, it is preferable to approach a nominal pore size of 0.1 micron, because as the nominal pore size decreases, the higher the log reduction of bacteria and the better the performance of the filter cartridge as a bactericidal device.

Perhaps the primary factor limiting flow of water through the above described filters is the total surface area of the membrane through which water is able to pass or more specifically, the lack of surface area. When a semipermeable membrane is in the form of a flat sheet, as is typically utilized in a microfiltration filter cartridge, the maximum surface area is limited to the circumference of the plastic or activated carbon core over which it is wrapped. One method to increase surface area is to pleat the filter medium as is done in purely mechanical membrane filters, such as automobile oil filters. In the microfiltration context this solution is difficult to implement.

In short, a need exists for a reverse osmosis water filter that is capable of retaining and eliminating bacteria and allowing sufficient fluid flow and water pressure to be of practical use in water systems around the world.

OBJECTS OF THE INVENTION

It is the principal object of this invention to provide a water filter that achieves a high level of separation of water soluble contaminants.

It is also an object of this invention to provide a water filter that resists fouling due to bacterial growth.

It is another object of this invention to provide a microfiltration filter capable of increased fluid flow.

It is a further object of this invention to provide a microfiltration filter that may be effectively utilized in low pressure water systems.

SUMMARY OF THE INVENTION

The present invention is directed toward an antimicrobial filter cartridge which utilizes a bundle of semipermeable hollow fibers centrally located within a housing. The housing has two chambers separated by a barrier through which the hollow fibers extend. The hollow fibers are enclosed in one chamber and open in the other.

The chamber housing the enclosed hollow fibers also contains a microporous filter medium, such as a melt blown polymer web or a tightly wound yarn, that surrounds the hollow fibers. This chamber also receives the fluid to be filtered. The barrier between the two chambers forces the water through the microporous filter medium where solid contaminates are removed. The water is also forced through the walls of the semipermeable hollow fibers which work to remove various dissolved solids from the water.

The water that enters the hollow fibers flows within the hollow fiber and through the barrier where it is then discharged into the other chamber of the housing from where it flows out of the housing and to its end use.

The various components of the antimicrobial filter, such as the hollow fibers and the microporous filter medium, may be treated with an antimicrobial agent to eliminate any microorganisms, such as bacteria, that may be filtered from the water.

BRIEF DESCRIPTION OF THE DRAWINGS

The foregoing and other objects will become more readily apparent by referring to the following detailed description and the appended drawings in which:

FIG. 1 is a cross-sectional view of one embodiment of an antimicrobial filter in accordance with the invention.

FIG. 2 is a cross-sectional view of a second embodiment of an antimicrobial filter in accordance with the invention.

DETAILED DESCRIPTION

In the following description, like reference numerals designate like or corresponding parts throughout the several figures. It is to be also understood that such terms as "front", "rear", "side", "up", and "down" are used for purposes of locating one element relative to another and are not to be construed as limiting terms. Further, it should be understood that the illustrations are for the purpose of describing preferred embodiments of the invention, and thus are not intended to limit the invention in any manner.

One aspect of the present invention is an improvement upon the bactericidal filters described in U.S. Pat. No. 5,762,797 (the '797 patent) and U.S. application Ser. No. 08/877,080 (the '080 application). In general terms, a filter cartridge is provided that is similar to the cartridges disclosed in the '797 patent and the '080 application except that the flat semipermeable membranes utilized in those cartridges is replaced with hollow fiber membranes. The hollow fiber membranes utilized in this application can be used with or without treatment with an antimicrobial agent, such as Microban® Additive B, but the use of such an antimicrobial agent is preferred. A description of hollow fiber membranes and their method of manufacture may be found in U.S. Pat. No. 5,762,798 to Wenthold et al., which is hereby incorporated by reference.

In order to aid in the understanding of this application a brief introduction to hollow fiber membranes is necessary. A microporous hollow fiber is a polymeric tube having an outside diameter less than or equal to 2 mm and whose wall functions as a semipermeable membrane. These microporous hollow fibers can be created with controlled porosity starting from as low as 0.05 micron to slightly less than 1 micron using techniques that are familiar to those well versed in the art. See Cabasso, "Hollow Fiber Membranes", Kirk-Othmer Encyclopedia & Chemical Technology, 3rd Ed., John Wiley & Sons, 12:492–517 (1984).

Hollow fiber membranes are made with many types of synthetic polymers such as acrylonitrile, polysulfone, polyethersulfones, aromatic polyamides, polyimides, polyamide-imides, and polyvinylidene fluoride. The preparation of membranes for diverse applications is extensively described in the patent and technical literature, some of the relevant patents being, Klein et al U.S. Pat. No. 4,051,300 and Wenthold et al U.S. Pat. No. 5,762,798. Also see "Hollow Fiber Membranes", Kirk-Othmer Encyclopedia of Chemical Technology, 3d Ed., John Wiley & Sons 12:492–517 (1984) all of which are incorporated herein by reference. Preferably, the hollow fibers utilized in the invention are treated with an antimicrobial agent. Preferably, the antimicrobial agent is selected from the group consisting of 2,4,4'-trichloro-2'hydroxy diphenol ether and 5-chloro-2-phenol(2,3-dichlorophenoxy). The antimicrobial agent is present in a concentration from about 500 ppm to about 20,000 ppm by weight, and preferably from about 2,500 ppm to about 20,000 ppm by weight based upon the weight of the polysulfone and polyvinylidene fluoride polymer. The antimicrobial agent is incorporated into hollow fibers by adding it to the "dope" solution used to form the hollow fibers. A wide variety of hollow fiber membranes may be made depending on their applications which include, reverse osmosis, ultrafiltration, microfiltration, etc. Although the concepts of the present invention apply equally to all three of these areas, this discussion is directed primarily to the area of microfiltration.

By using bundles of these microporous hollow fibers as a membrane instead of a flat sheet microporous membrane, it is possible to increase the available filter surface area within a filter cartridge of the same dimension by several orders of magnitude. For example, in the conventional 10 inch filter cartridge design described in the '797 patent and the '080 application, the surface area of the flat sheet membrane is approximately 0.04 $m^2$. In a filter cartridge of the same basic design using hollow fibers, it is possible to achieve a microporous membrane surface area of between 60 to 160 $m^2$ or more depending on the diameter of the hollow fibers utilized. Availability of such a large surface area results in higher flow rates, lower back pressures and the ability to use lower pore diameters resulting in higher bacterial log reduction.

The present improvement in design of bactericidal filter cartridges, such as those described in the '797 patent and the '080 application consists of substituting a microporous hollow fiber membrane for a flat sheet microporous membrane. This substitution allows the use of membranes with much finer pore diameters without compromising flow rates or creating unacceptable back pressure.

FIG. 1 illustrates a preferred embodiment of an antimicrobial filter cartridge 10 constructed in accordance with the present invention. The antimicrobial filter cartridge 10 includes a plurality of semipermeable hollow fibers 12 centrally located within housing 14 which has a first chamber 16 and a second chamber 18 separated by a barrier 20 through which hollow fibers 12 extend. The second chamber 18 is in fluid communication with the source of the fluid to be filtered through fluid inlet 24. For purposes of this discussion water will be used as the fluid to be filtered. The first chamber 16 acts as a temporary repository of filtered water.

The semipermeable hollow fibers 12 may be made of any of the types of synthetic polymers discussed above and incorporated by reference including acrylonitrile, polysulfone, polyethersulfones, aromatic polyamides, polyimides, polyamide-imides, and polyvinylidene fluoride. Preferably the hollow fibers 12 also incorporate an antimicrobial agent. Preferably, the antimicrobial agent used to treat the hollow fibers, and any other component of the filter, is practically insoluble in the water passing through and over the filter cartridge, and is safe, non-toxic, non-carcinogenic, non-sensitizing to human and animal skin and does not accumulate in the human body when ingested. Generally, therefore, the antimicrobial is a broad spectrum antimicrobial agent, i.e., it is equally effective against the majority of harmful bacteria encountered in water. For example, an antimicrobial agent such as 2,4,4'-trichloro-2'-hydroxydiphenol ether, or 5-chloro-2phenol (2,4 dichlorophenoxy) commonly sold under the trademark MICROBAN®B, by Microban Products Co., Huntersville, N.C., typically will be used. However, it will be understood various other antimicrobial agents that are safe non-toxic and substantially insoluble in water can be used in the present invention.

Hollow fibers formed of polyvinylidene fluoride (pvd) containing Microban® B have been tested and found to exhibit excellent antimicrobial properties as shown in the test results below.

| MICROBIOLOGICAL TEST REPORT Kirby Bauer | | |
|---|---|---|
| Test Organism: | Syaphylococcus aureus ATCC 6538 Escherichia coli ATCC 25922 | |
| Sample Material: | PVDF | |
| Sample Size: | Variable | |
| Growth Medium: | Mueller-Hinton Agar | |
| Test Conditions: | Incubated at 37° ± 2° C. for 18–24 hours | |
| | Results (Zone Size) | |
| Sample Identification | S. aureus | E. coli |
| 7196-OCP-TP-1 (1.92) Microban in dope | 19 mm | 12 mm |
| 7197-OCP-TP-1 (0.98) Microban in dope | 17 mm | 10 mm |
| 7198-OCP-TP-1 (0.48) Microban in dope | 14 mm | 9 mm |

Interpretation of Results
NZ = No Zone of inhibition surrounding the sample
NI = No Inhibition of Growth Under the Sample
I = Inhibition of Growth Under the Sample (If Observable)
mm = Zone of Inhibition Reported in Millimeters The hollow fibers 12 should be arranged such that an open end extends from the barrier 20 into the first chamber 16 while a closed end extends from the barrier 20 into the second chamber 18. Such an arrangement may be accomplished by enclosing one end of a single hollow fiber 12 and extending that end of the hollow fiber 12 into the second chamber 18. A similar arrangement may be accomplished by bending a hollow fiber 12 that has both ends open. This second possibility is illustrated in FIG. 1. In FIG. 1 the hollow fibers 12 are long open-ended tubes that are bent such that the two ends are approximately parallel and approximately equidistant from a midpoint. The hollow fibers 12 must not be bent so as to compromise their structural integrity. The hollow fibers 12 are bundled together by the barrier 20 and placed centrally within housing 14 such that the open end portions of the hollow fibers 12 extend into the first chamber 16.

Preferably the barrier 20 is formed of a thermoset or thermoplastic polymer such as polyurethane or an epoxy. The barrier 20 which encloses a portion of the hollow fibers 20 may be manufactured external to the housing. It is anticipated that in most instances the barrier 20 enclosing hollow fibers 12 will be formed in a mold external to the housing so that other elements may be more easily secured through placement within the barrier 20 as will be discussed below.

Continuing with FIG. 1, surrounding the bundle of hollow fibers 12 is a microporous filter medium. In FIG. 1 the microporous filter medium is a melt-blown polymer web 22. The polymer may be selected from the group consisting of nylon, polypropylene, cellulose acetate, rayon, lyocell, acrylic, polyester, polyethylene and mixtures thereof. In a preferred embodiment polypropylene fibers are impregnated with Microban® B during extrusion and blown into a continuous web having an effective pore size of 5 microns. The concentration of the antimicrobial agent in the fibers generally is between 50 to 20,000 ppm, preferably between 1000 ppm to 5000 ppm.

The melt blown web 22 may be held in place by making it of sufficient thickness such that the sides of housing 14 keep its position secure. In fact it is important to surround the hollow fibers 12 and all the empty volume near them with antimicrobial fibers because the objective is to force all bacteria mechanically withheld by the microporous filter medium to come into contact with an antimicrobial surface so that the bacteria may be deactivated. Alternatively and as illustrated in FIG. 1 the melt blown web 22 may be secured by setting one end of the web within barrier 20 thereby making the barrier 20, the bundle of hollow fibers 12 and the melt blown web 22 a single unit within housing 14.

In operation water enters antimicrobial filter cartridge 10 second chamber 18 through fluid inlet 24 and is prohibited from flowing into the first chamber 16 by the barrier 20. The barrier 20 along with the walls of the second chamber 18 force the water into contact with the melt blown web 22 and the semipermeable walls of the hollow fibers 12 where the fluid is filtered and any retained microorganisms, such as bacteria, are eliminated by coming into contact with the antimicrobial agent.

The water that passes through the semipermeable walls of the hollow fibers 12 and into the annular space within each hollow fiber 12 then exits the hollow fiber 12 into the first chamber 16 and is discharged out of fluid outlet 26. The filtering capability of such a filter should meet that of the filters described in the '797 patent and the '080 application while operating at higher flow rates and reduced back pressure.

FIG. 2 illustrates another preferred embodiment of the antimicrobial filter according to the invention that is very similar to FIG. 1. However in this embodiment the melt blown web 22 is replaced by a wrapping of yarn 28. The yarn can be made of cotton, nylon, polypropylene, cellulose acetate, rayon, lyocell, acrylic, polyester, polyethylene or any mixture thereof. In a preferred embodiment shown in FIG. 2, the yarn 28 is 0.60 cotton count (cc) yarn. The yarn 28 contains polypropylene fiber between 0.3 denier per filament (dpf) to 10 dpf, the preferable range based on cost and performance being 1.5 dpf to 6 dpf. The polypropylene fiber is cut into 2 inch staple, then opened and carded and friction spun into a 0.60 cc yarn. The polypropylene fiber is impregnated with an antimicrobial agent, such as Microban® Additive B during extrusion. The concentration of the antimicrobial agent in the fibers generally is between 50 to 20,000 ppm, preferably between 1000 ppm to 5000 ppm. The 0.60 cc yarn is tightly wound around the hollow fibers 12 in a spiral pattern to cover the bundle of hollow fibers 12 completely and to give an effective pore size of 1–5 $\mu$. The yarn 28 may also be wrapped in a criss-cross pattern as is well described in the '797 patent and the '080 application.

Due to the fragile nature of the hollow fibers 12, it is recommended that the yarn 28 be wrapped around a ridged guide 30 which is set in the barrier 20 and which surrounds and is in very close proximity to the bundle of hollow fibers 12. The guide 30 may simply consist of two or more poles situated at the edge of the bundle of hollow fibers 12 as shown in FIG. 2 or it may be a perforated cylindrical object that completely encloses the bundle of hollow fibers 12.

In an additional embodiment of the antimicrobial filter according to the invention, it is possible to have an activated carbon core working in conjunction with the semipermeable hollow fibers 12. For example, the hollow fibers 12 could be situated within a core of granulated activated carbon which is in turn surrounded by a microporous filter medium. Likewise the hollow fibers 12 could surround a core of activated carbon. If activated carbon is utilized it is preferable that it be treated with an antimicrobial agent as is thoroughly discussed in the '797 patent and the '080 application.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, the intellectual property rights to the invention are defined only by the following claims and reasonable extensions and equivalents thereof.

SUMMARY OF THE ACHIEVEMENTS OF THE OBJECTS OF THE INVENTION

From the foregoing, it is readily apparent that I have invented an antimicrobial filter cartridge that achieves a high level of separation of water contaminants while simultaneously resisting fouling due to bacterial growth. Furthermore, the design of the antimicrobial filter cartridge according to the invention provides a microfiltration filter cartridge capable of increased fluid flow and that may be effectively utilized in low pressure water systems.

What is claimed is:

1. An antimicrobial filter cartridge comprising:
   a plurality of semi-permeable hollow fibers, said hollow fibers being open at one end and comprising a non-metallic antimicrobial agent, and
   at least one layer of a microporous filter medium wrapped around said hollow fibers.

2. The antimicrobial filter cartridge of claim 1 wherein said microporous filter medium is a melt blown polymer web formed from the group consisting of nylon, polypropylene, cellulose acetate, rayon, lyocell, acrylic, polyester, polyethylene and mixtures thereof.

3. The antimicrobial filter cartridge of claim 1 wherein said microporous filter medium is a yarn wound about said hollow fibers.

4. The antimicrobial filter cartridge of claim 3 wherein said yarn is made from cotton or a polymer selected from the group consisting of nylon, polypropylene, cellulose acetate, rayon, lyocell, acrylic, polyester, polyethylene and mixtures thereof.

5. The antimicrobial filter cartridge of claim 2 wherein said melt blown polymer web further comprises an antimicrobial agent incorporated therein.

6. The antimicrobial filter cartridge of claim 3 wherein said yarn is wound in a spiral winding in such manner that each winding turn of said yarn contacts its adjacent turns.

7. The antimicrobial filter cartridge of claim 3 wherein said yarn is wound in a criss-cross pattern.

8. The antimicrobial filter cartridge of claim 3 wherein said yarn further comprises an antimicrobial agent.

9. The antimicrobial filter cartridge of claim 1, wherein said antimicrobial agent is selected from the group consisting of 2,4,4-trichloro-2-hydroxy diphenol ether and 5-chloro-2-phenol (2,4 dichlorophenoxy) compounds.

10. The antimicrobial filter cartridge of claim 1 wherein said hollow fibers have a nominal pore size of from about 0.01 micron to about 1.0 micron.

11. The antimicrobial filter cartridge of claim 1 wherein said hollow fibers have a nominal pore size of from about 0.1 micron to about 0.75 micron.

12. An antimicrobial filter cartridge comprising, activated carbon and a plurality of semi-permeable hollow fibers in close proximity to said activated carbon, said hollow fibers being open at one end and comprising a non-metallic antimicrobial agent; and at least one layer of a microporous filter medium wrapped around said plurality of hollow fibers.

13. The antimicrobial filter cartridge of claim 12, wherein said antimicrobial agent is selected from the group consisting of 2,4,4-trichloro-2-hydroxy diphenol ether and 5-chloro-2-phenol(2,4 dichlorophenoxy) compounds.

14. The antimicrobial filter cartridge of claim 12 wherein said activated carbon is treated with an antimicrobial agent.

15. The antimicrobial filter cartridge of claim 12 wherein said microporous filter medium is a melt blown polymer web formed from the group consisting of nylon, polypropylene, cellulose acetate, rayon, lyocell, acrylic, polyester, polyethylene and mixtures thereof.

16. The antimicrobial filter cartridge of claim 12 wherein said microporous filter medium is a yarn wound about said hollow fibers.

17. The antimicrobial filter cartridge of claim 16 wherein said yarn is made from cotton or a polymer selected from the group consisting of nylon, polypropylene, cellulose acetate, rayon, lyocell, acrylic, polyester, polyethylene and mixtures thereof.

18. The antimicrobial filter cartridge of claim 15 wherein said melt blown polymer web further comprises an antimicrobial agent.

19. The antimicrobial filter cartridge of claim 16 wherein said yarn is wound in a spiral winding such that each winding turn of said yarn contacts its adjacent turns.

20. The antimicrobial filter cartridge of claim 16 wherein said yarn is wound in a criss-cross pattern.

21. The antimicrobial filter cartridge of claim 16 wherein said yarn further comprises an antimicrobial agent.

22. The antimicrobial filter cartridge of claim 12 wherein said hollow fibers have a nominal pore size of from about 0.01 micron to about 1.0 micron.

23. The antimicrobial filter cartridge of claim 12 wherein said hollow fibers have a nominal pore size of from about 0.1 micron to about 0.75 micron.

24. A semi-permeable hollow fiber filter system comprising a plurality of polymer fibers surrounded by a microporous filter medium, and enclosed within a housing, said polymer fibers being generally cylindrical and having an outer wall and an inner wall thereby defining an annular space within each of said polymer fibers, said annular space being in fluid communication with the outside of the housing, said polymer fibers further comprising a non-leaching non-metallic antimicrobial agent disbursed throughout said polymer fiber.

* * * * *